United States Patent [19]

Yeung et al.

[11] Patent Number: 5,580,923
[45] Date of Patent: Dec. 3, 1996

[54] ANTI-ADHESION FILMS AND COMPOSITIONS FOR MEDICAL USE

[75] Inventors: Jeffrey E. Yeung, San Jose; George H. Chu, Cupertino; Frank A. DeLustro, Belmont; Woonza M. Rhee, Palo Alto, all of Calif.

[73] Assignee: Collagen Corporation, Palo Alto, Calif.

[21] Appl. No.: 403,360

[22] Filed: Mar. 14, 1995

[51] Int. Cl.$^6$ ............... C08G 63/48; C08G 63/91; A61F 2/00
[52] U.S. Cl. ............... 525/54.1; 523/105; 523/113; 602/50; 602/52
[58] Field of Search ............... 525/54.1; 523/105, 523/113; 530/356; 602/50, 52

[56] References Cited

U.S. PATENT DOCUMENTS

| | | | |
|---|---|---|---|
| 4,704,131 | 11/1987 | Noishiki et al. | 623/66 |
| 5,162,430 | 11/1992 | Rhee et al. | 525/54.1 |
| 5,364,622 | 11/1994 | Franz et al. | 424/94.64 |

FOREIGN PATENT DOCUMENTS

0431479A1  6/1991  European Pat. Off. ............... 15/32

OTHER PUBLICATIONS

G. Pados, M.D. et al., "Adhesions", *Current Opinion in Obstetrics and Gynecology*, 4:421–18 (1992).
V. Gomel, M.D. et al., "Infertility Surgery: Microsurgery", *Current Opinion in Obstetrics and Gynecology*, 4:390–99 (1992).
B. Urman, M.D. et al., "Effect of Hyaluronic Acid on Postoperative Intraperitoneal Adhesion Formation and Reformation In the Rat Model", *Fertility and Sterillity*, vol. 56, No. 3, pp. 568–570 (1991).
T. Tulandi, M.D., "Effects of Fibrin Sealant on Tubal Anastomosis and Adhesion Formation", *Fertility and Sterility*, vol. 56, No. 1, pp. 136 138 (1991).
N. Fleisher et al., "Regeneration of Lost Attachment Apparatus in the Dog Using Polygalactin–910", *J. Dent. Res.*, 66 Spec. Issue Mar., vol. 281, Abstract 1393 (1987).
K. Pagidas, M.D. et al, "Effects of Ringer's Lactate, Interceed (TC7) and Gore–Tex Surgical Membrane on Postsurgical Adhesion Formation", *Fertility and Sterility*, vol. 57, No. 1, pp. 199–201 (1992).
A. Steinleitner, M.D. et al, "Poloxamer 407 as an Intraperitoneal Barrier Material for the Prevention of Postsurgical Adhesion Formation and Reformation in Rodent Models for Reproductive Surgery", *Obstetrics and Gynecology*, 77:48–52 (1991).

*Primary Examiner*—Nathan M. Nutter
*Attorney, Agent, or Firm*—Laurie A. Axford; Shirley L. Church; Wilhelmus J. Wytenburg

[57] ABSTRACT

Anti-adhesion films useful for the prevention of surgical adhesions are disclosed. These films comprise substrate materials (such as collagen) and hetero-bifunctional anti-adhesion binding agents, wherein the substrate material is covalently linked to receptive tissue within the body of a patient via the binding agent. Preferred binding agents comprise substrate-reactive and tissue-selective functional groups. Anti-adhesion compositions useful for the formation of such films are also disclosed.

24 Claims, 9 Drawing Sheets

(12)

(13)

(6)

(7)

(8)

(14)
(COLD)

(15)

X = I, Br, Cl (21)

(22)

ANTI-ADHESION FILMS AND COMPOSITIONS FOR MEDICAL USE

FIELD OF THE INVENTION

This invention relates to the field of thin films and, more particularly, relates to thin films for use in medical application, specifically in the prevention of adhesions. The anti-adhesion films of the present invention comprise at least one layer of substrate material, such as collagen, covalently bonded to a receptive tissue of a patient.

BACKGROUND OF THE INVENTION

The mechanism of adhesion formation represents a variation of the physiological healing process wherein vital tissues, usually different tissues, adhere to one another in an undesirable fashion. See, for example, Pados et al., 1992, *Current Opinion in Obstetrics and Gynecology*, 4:412–18.

For example, increased permeability of blood vessels as a result of a peritoneal injury produces a serosanguinous, proteinaceous exudate that quickly coagulates, forming a fibrinous material that first plugs the defective area, and which is further infiltrated by inflammatory cells. If this fibrinous mass is not dispersed by fibrinolysis, fibroblasts and blood vessels invade, resulting in organization and formation of adhesions.

Pelvic or abdominal adhesions, a frequent occurrence after abdominal surgery and inflammatory processes such as infections and endometriosis, represent a major cause of female infertility. Such adhesions further increase intraoperative complications, constitute a major cause of small bowel obstructions, and have been implicated in the pathogenesis of chronic pelvic pain.

Vital tissues, such as blood vessels or organs including the kidney, liver, and intestines, are coated with mucous membranes or serous membranes so that they can function independently of each other. Surgical operations or inflammation in those portions of the body coated with serous membranes could result in adhesion between these and adjacent tissues.

In the field of orthopedics, acute or chronic arthritis such as suppurative, gonorrheal, tuberculous or rheumatoid arthritis, or traumatic injuries at a joint (such as fractures or sprains) would result in ankylotic diseases wherein the surface of the bones constituting the joint adhere to each other and thereby restrict the mobility of the joint. Congenital radioulnar synostosis, wherein the radius and ulna adhere together, is difficult to remedy by a surgical operation, as the separated bones would frequently re-adhere.

When neural spine and spinal cord are removed dorsally by a surgical operation in a vertebral canal cavity in treating myeloma, intervertebral hemia, or adhesive spinal meningitis, it is necessary to prevent adhesion to the body wall.

Suturing of ruptured tendons and tendon transfer would sometimes fail because of the post-operative adhesion of the tendon to the scar in the skin. Furthermore, in the case of rupture of a flexor tendon between a metacarpophalangeal joint and a proximophalangeal joint, the function of the finger would not recover by the intermittent suture of musculus flexor digitorum superficialis and musculus flexor digitorum profundus, as these tendons, if injured simultaneously, would adhere to one other. Therefore, is also necessary to prevent adhesion between the two tendons in this case.

In the field of thoracosurgery, bronchi dilated by primary diseases, such as pulmonary or suppurative diseases, would allow the extension of inflammation over the surrounding pulmonary parenchyma and the formation of a suppurative focus, thereby resulting in adhesion to the pleura. In addition, lung cancer would result in adhesion to the body wall.

In the field of abdosurgery, external damages, such as disjunction or rupture by a severe impact, or morbid damages such as inflammation or tumor in organs in an abdominal cavity, including liver, kidney, pancreas, spleen and intestine, would result in adhesion of organs to each other or of an organ to the abdominal wall. Rupture of the diaphragm or peritoneum caused by severe external closed damage would result in adhesion of an organ to the abdominal wall. Further, ileus of the small or large intestine, which has the same meaning as intestinal obstruction and generally refers to an acute obstruction, would be mainly caused by adhesive ileus, wherein the intestinal cavity is closed by a crooked or flexed intestinal tract resulting from adhesion in the abdominal cavity, most of which would be formed post-operatively. Therefore, it is necessary to prevent adhesion in the abdominal cavity after the operation to prevent said adhesive ileus. Abdominal abscess could sometimes result in adhesion of peritoneum, diaphragm, or pleura to each other. In addition, adhesion between adjacent organs, or of an organ to the abdominal wall, should be prevented in the case of various diseases or tumors which cannot be removed completely in internal organs.

In the field of obstetrics and gynecology, endometritis, excessive artificial abortions, or intra-uterine curettage would sometimes result in partial or whole adhesion of the placenta to the uterine wall, making separation of the placenta at delivery difficult. Adhesion formation following infertility surgery, such as microsurgery, reconstructive tubal surgery, laparotomy and laparoscopy, remains a significant cause for failure of conception. For example, adhesions which encapsulate the ovary or the distal oviduct, or which distort the normal relationship that exists between the ovary and the oviduct, may interfere with fertility by preventing or impeding ovum pick-up. See, for example, Gomel et al., 1992, *Current Opinion in Obstetrics and Gynecology*, 4:390–99. Furthermore, cancerous tissues found in breast cancer multiply remarkably and may adhere to adjacent skin or a tendon.

In the field of brain surgery, adhesive arachnitis would be induced by chronic or suppurative intracranial inflammation (resulting from an unknown primary cause, syphilis, tuberculosis, or the like), intrathecal injection of medicine in therapy, or myelography.

In addition, adhesions resulting from facial palsy caused by a malignant tumor in the salivary gland would sometimes restrict mobility. A cancerous cervical lymph node adheres to the surrounding tissues to thereby restrict mobility.

In the field of ophthalmology, ocular surgery involving the musculature, ligaments, glands, and nerve tissue may generate post-operative adhesions.

Similarly, periodontal surgery may result in post-operative adhesions between soft and hard tissues of the mouth and throat, such as the palate, gums, teeth, and bone (such as the jawbone).

As described above, adhesion of vital tissues, large or small, may be observed in most of the surgical fields. Adhesion formation may occur for various reasons, including mechanical and chemical stimulation of vital tissues accompanying surgical operations, post-operative bacterial infection, inflammation, or complications. Additional factors, such as foreign body reactions, hemorrhages, and endometriosis may influence adhesion formation.

It is thus desirable to prevent the formation of adhesions, particular post-operative adhesions. A number of preventative methods have been developed. Effective adjuvants for the prevention or reduction of post-operative adhesions continue to elude the surgeon, and new substances are being experimented with.

Initially, drugs or adhesion-inhibiting agents, such as steroids, polyvinyl-pyrrolidone (PVP), chondroitin sulfuric acid, or an aqueous solution of sodium alginate, were administered, usually at the wound site, to minimize adhesion formation. For example, the efficacy of hyaluronic acid solution on postoperative adhesion formation in rat models has been found to be minimal (see Urman et al., 1991, *Fertil. Steril.*, 56:568–70). However, success was limited, as the effects were neither constant nor perfect. Additionally, water-soluble adhesion-preventing agents may enter normal regions entirely irrelevant to the operation, thereby possibly causing, rather than preventing, adhesion. Additionally, use of fibrinolytic agents, anti-coagulants, anti-inflammatory agents, and antibiotics has been attempted with limited success.

Early methods for mechanical separation of tissues included the use of materials such as dextran, mineral oil, silicone, providine, vaseline, crystalloid solutions, and carboxymethylcellulose.

Physical barriers mechanically separate the opposed surfaces and exert their protective action, at least partly, because they remain in place beyond a crucial point (often, about 3 days), at which time competition of fibrinolytic activity and fibrosis will determine the formation of adhesions. Physical barriers, including those of endogenous tissue (such as omental grafts, peritoneal grafts, bladder strips, and fetal membranes such as amniotic membranes), and exogenous material (such as oxidized cellulose, oxidized regenerated cellulose, gelatin, rubber sheets, metal foils, and plastic hoods) have long been used, but with little success.

Non-resorbable membranes, such as Goretex® (PTFE; polytetrafluoroethylene) sheets or membranes, Silastic® (a medical grade silicone elastomer produced by Dow Corning), and Millipore® filter barriers, are advantageous in that they remain intact long after implantation and thus play the role of barrier perfectly, but are disadvantageous in that they require two surgical interventions: first to apply the membrane (using sutures or adhesives), and second to remove the membrane 4 to 6 weeks after the initial surgery.

Artificial biodegradable (e.g., resorbable) membranes, such as Gelfoam® (an absorbable collagen foam or sponge produced by Upjohn), have also been used. Terao et al. (European Patent Application No. 431479, published 12 Jun. 1991 ) describe a collagen-chitin membrane for wound-covering and adhesion prevention. Although such resorbable materials alleviate the need for a second surgical intervention, they are less than perfect in view of undesirably rapid rates of resorption and the often substantial concomitant inflammatory response.

The anti-adhesion properties of fibrin glue (produced by Tisseel, Canada) were examined and found to yield results similar to those observed for sutures (see Tulandi, 1991, *Fertil. Steril.*, 56: 136–38). An alternative material, Vicryl® (polygalactin-910), is a slowly resorbable, biocompatible, tightly woven mesh graft which has been used as a dural substitute in neural surgery (see Fleisher et al., 1987, *J. Dent. Res.* 66 (Spec. Issue Mar.), Vol. 281, Abstract 1393). Both Interceed® and Surgicel® (produced by Johnson & Johnson), fabrics composed of oxidized regenerated cellulose (the former includes the anticoagulant, heparin), have been studied in connection with adhesion formation in a rat uterine horn model (see Pagidas et al., 1992, *Fertil. Steril.*, 57:933–38). Poloxamer 407® (produced by Mediventures, Inc.) is representative of a group of polymers which exist as liquids at room temperature, but which form a solid gel at body temperature. Such materials have been shown to have anti-adhesion properties in rats (for pelvic wounds) and rabbits (see Steinleitner et al., 1991, *Obstet. Gynecol.*, 77:48–52).

One key disadvantage of the physical barriers currently available involves the method of attachment. In order to prevent the formation of adhesions, anti-adhesive adjuvants must remain in place for a required period of time. As the tissues to be separated are often somewhat mobile, especially relative to adjacent or overlying tissue (for example, abdominal linings, abdominal organs, tendons, and the like), it is necessary to ensure that the adjuvant remains both intact and in place. Methods of attachment, such as suturing (for example, with microsutures) and biocompatible adhesive glues have been used, but with limited success. The attachment of sutures themselves (for example, by stitching) causes surgical trauma and additional potential for adhesion formation. In addition, sutures and adhesives often provide imperfect attachment, and the adjuvant tears, rips, or is otherwise freed from the attachment points, and is thereby unable to perform an anti-adhesion function.

It is therefore an object of the invention to provide compositions and methods for preventing the formation of adhesions. It is another object of the invention to provide new adhesion preventatives which are resorbable and which therefore do not require surgical intervention for removal. It is yet another object of the invention to provide adhesion preventatives, in the form of anti-adhesion-films, which reduce or remove the need for mechanical means, such as sutures or adhesive tape, for attachment or to ensure immobility. It is still another object of the present invention to provide new anti-adhesion films which have, in combination with anti-adhesion properties, wound-healing and hemostasis-preventative functions.

SUMMARY OF THE INVENTION

The anti-adhesion compositions of the present invention, useful in the formation of anti-adhesion films (devices), comprise a substrate material and an anti-adhesion binding agent. In a preferred embodiment, the substrate material comprises collagen. In another preferred embodiment, the binding agent comprises at least one tissue-selective functional group and at least one substrate-reactive functional group. In yet another preferred embodiment, the tissue-selective group is a sulfhydryl-selective functional group. In still another preferred embodiment, the binding agent comprises a derivative of polyethylene glycol.

The anti-adhesion films (devices) of the present invention comprise at least one layer of substrate material covalently bonded to receptive tissue of a patient via an anti-adhesion binding agent. More specifically, the anti-adhesion devices of the present invention comprise at least one layer of substrate material covalently bonded to receptive tissue of a patient. The device has been formed upon the chemical reaction of the substrate material and receptive tissue with the anti-adhesion binding agent. In a preferred embodiment, the binding agent comprises at least one tissue-selective functional group and at least one substrate-reactive functional group, wherein at least a portion of said tissue-selective groups have chemically reacted with said receptive tissue to form covalent linkages, and at least a portion of said substrate-reactive groups have chemically reacted with said substrate material to form covalent linkages.

The anti-adhesion methods of the present invention involve the formation of anti-adhesion devices for the prevention of adhesions.

DETAILED DESCRIPTION OF THE PREFERRED EMBODIMENTS OF THE INVENTION

Figure 1:
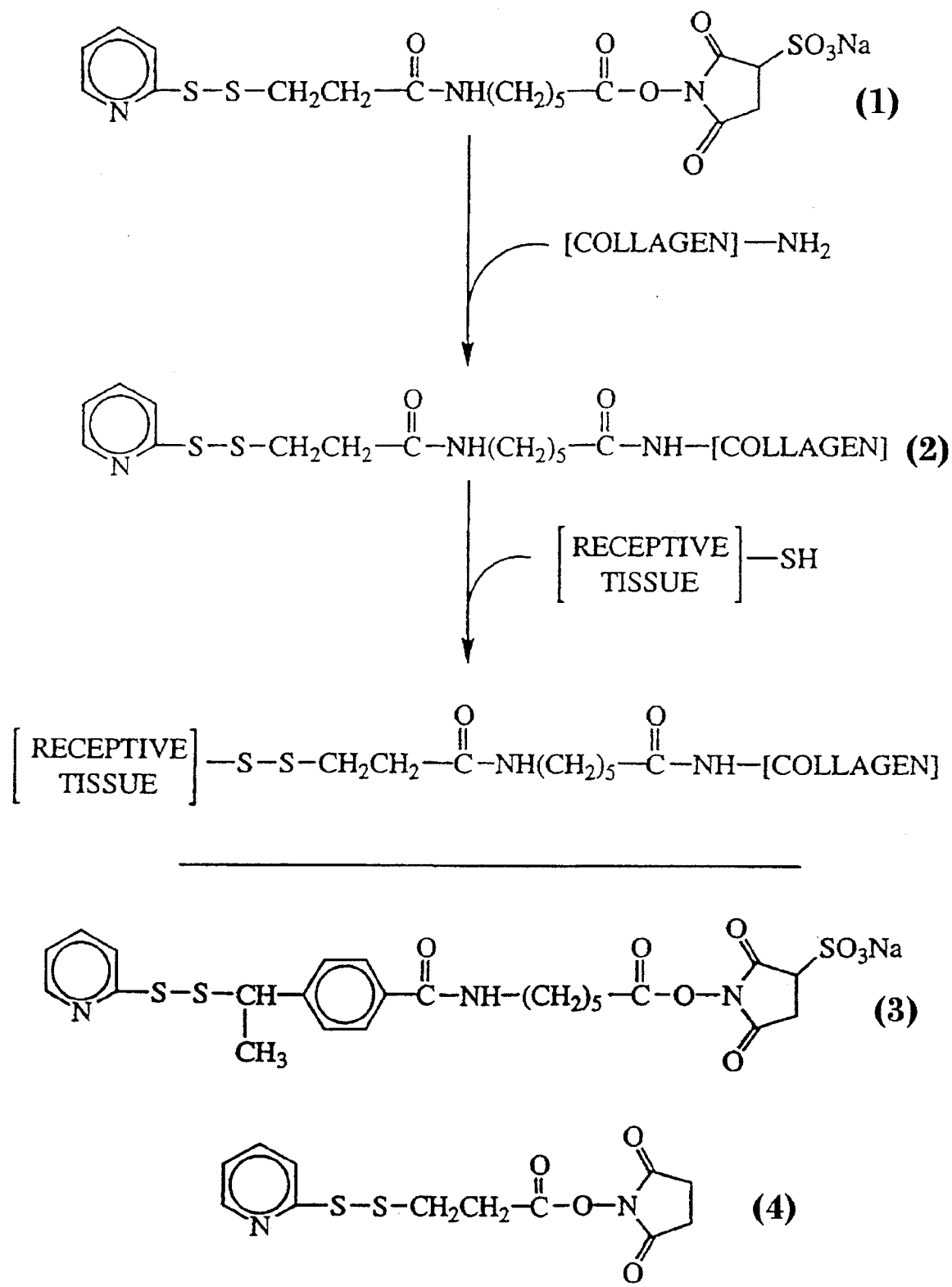
FIG. 1 is a flow chart which illustrates the preparation and use of an anti-adhesion composition comprising collagen and the anti-adhesion binding agent sulfo-LC-SPDP.

Before the anti-adhesion compositions and films, and methods for their preparation and use, are described, it is to be understood that this invention is not intended to be limited to the particular compositions, films, and methods described in the preferred embodiments, as one skilled in the art can extend the concepts involved using variations which are obvious after reading the present disclosure.

It must be noted that, as used in this specification and the appended claims, the singular forms "a", "an", and "the" include plural referents, unless the context clearly dictates otherwise. Thus, for example, reference to "a heterobifunctional binding agent" includes mixtures of binding agents, reference to "a substrate material" includes mixtures of substrate materials, and reference to "a substrate-reactive functional group" includes one or more such groups, which may be the same or different.

Unless defined otherwise, all technical and scientific terms used herein have the same meaning as commonly understood by one of ordinary skill in the art to which this invention belongs. Although any methods and materials similar or equivalent to those described herein may be useful in the practice or testing of the present invention, preferred compositions, films, methods and materials are described below. All patents and publications mentioned herein are incorporated herein by reference to disclose and describe the information they are cited in connection with. Specific terminology of particular importance to the description of the present invention is defined below.

The term "substrate material" as used herein relates to the primary structural component of the anti-adhesion membrane. The substrate material itself may or may not be crosslinked, for example, by hydrogen bonding, van der Waals bonding, or covalent bonding. Furthermore, substrate materials may be chemically crosslinked via covalent bonds introduced by, for example, exposure to radiation or reaction with crosslinking agents.

The term "anti-adhesion binding agents" as used herein relates to hetero-bifunctional binding agents which have at least one substrate-reactive functional group and at least one tissue-reactive functional group. Preferably, anti-adhesion binding agents have at least one substrate-selective functional group and at least one tissue-reactive functional group; or, at least one substrate-reactive functional group and at least one tissue-selective functional group. Still more preferably, anti-adhesion binding agents have at least one substrate-selective functional group and at least one tissue-selective functional group. Most preferably, anti-adhesion binding agents have only substrate-selective and tissue-selective functional groups.

The term "anti-adhesion composition" or "anti-adhesion device" as used herein refers to a composition comprising substrate material and at least one anti-adhesion binding agent. Chemical reaction between said substrate material and binding agent (particularly, the functional groups thereof) to form a covalent linkage between the substrate material and the binding agent, may be incomplete, partially complete, or fully complete.

The term "hetero-bifunctional binding agents" as used herein relates to compounds which have two or more functional groups which are able to react chemically with, for example, functional groups of the substrate material or functional groups present in compounds found in receptive tissue to form covalent bonds, wherein at least two of said two or more functional groups are different.

The term "substrate-reactive functional groups" as used herein relates to functional groups which are able to react chemically with functional groups of the substrate material to form covalent bonds. The term "substrate non-reactive functional groups" as used herein relates to functional groups which are essentially unable to react chemically with functional groups of the substrate material to form covalent bonds. The term "substrate-selective functional groups" as used herein relates to functional groups which are essentially unable to react chemically with functional groups of compounds present in receptive tissue of a patient.

The term "functional groups which are able to react chemically" as used herein includes functional groups which can be activated or derivatized so as to be able to react chemically with, for example, functional groups of the substrate material or functional groups present in compounds found in receptive tissue, to form covalent bonds. The term "react chemically" is generic to reactions which proceed upon mixing (and, optionally, by adjusting conditions such as pH, temperature, salt concentration, and the like), and those which proceed upon irradiation (e.g., so-called photoactivated reactions).

The term "essentially unable to react chemically" as used herein describes functional groups for which reaction with other specified functional groups (for example, those of the substrate material or of compounds found in receptive tissue) is strongly disfavored owing to, for example, kinetic or thermodynamic criteria, and does not exclude those functional groups for which reaction is actually or theoretically possible, but for which such reaction is strongly disfavored under the chemical or physical conditions applied.

The term "strongly disfavored" as used herein to describe chemical reactions relates to reaction selectivity. Reactions which are strongly disfavored proceed to completion much less frequently (yielding undesired products or chemical linkages) than those which are strongly favored (yielding desired products or chemical linkages). Preferably, products of strongly favored reactions outnumber products of strongly disfavored reactions by 3:1, more preferably 4:1, still more preferably 5:1, yet more preferably 10:1, most preferably more than 10:1.

The term "tissue-reactive functional groups" as used herein relates to functional groups which are able to react chemically with functional groups of compounds present ine receptive tissue of a patient. The term "tissue non-reactive functional groups" as used herein relates to functional groups which are essentially unable to react chemically with functional groups of compounds present in receptive tissue of a patient. The term "tissue-selective functional groups" as used herein relates to tissue-reactive functional groups which are also substrate non-reactive functional groups; that is, functional groups which are essentially unable to react chemically with functional groups of the substrate material.

The term "receptive tissue" as used herein relates generally to tissues of the patient to which the anti-adhesion composition or membrane is applied and to which the anti-adhesion film will ultimately be chemically bound. Examples of receptive tissues include, but are not limited to, bones (such as those of fingers and hands, toes and feet, head and jaw, elbow, wrist, shoulder, sternum, knee, hip, pelvis, and spinal column), surface covering and musculature (such as skin, muscle, tendon, and ligament), vasculature (such as arteries and veins), sense organs (such as the eyes, nose, ears, tongue, and glands), upper chest organs (such as the larynx, lungs, heart, pleura, thyroid gland, thymus gland, peritoneum, and omenta), digestive organs (such as the trachea, stomach, duodenum, small intestine, large intestine, appendix, and colon), abdominal organs (such as the liver, kidney, pancreas, spleen, and bladder), and reproductive organs (such as the uterus, ovaries, fallopian tubes, and mammary glands).

The term "patient" as used herein relates to the animal or human to which the anti-adhesion composition is administered. Preferably, the patient is a mammal. More preferably, the patient is a human.

Examples of substrate materials include collagen, fibrin, glycosaminoglycans (for example, dermatan sulfate, hyaluronic acid, hyaluronate, chondroitin sulfates A, B, and C, chitin, and derivatives such as chitosan, heparin, heparin sulfate, keratin sulfate, and keratosulfate) and derivatives and mixtures thereof. Preferably, the substrate material comprises collagen, more preferably the substrate material comprises at least about 30% collagen by weight, still more preferably at least about 60% collagen by weight, yet more preferably at least about 90% collagen by weight. The substrate material may consist essentially of collagen with no other substrate-type materials present.

The term "collagen" as used herein is used in the conventional sense to describe a material which is the major protein component of the extracellular matrix of bone, cartilage, skin, and connective tissue in animals, and includes all forms of collagen, including native collagens which have been processed or otherwise modified and collagens that have been produced by genetic engineering (i.e., recombinant collagen).

Collagen in its native form is typically a rigid, rod-shaped molecule approximately 300 nm long and 1.5 nm in diameter. It is composed of three collagen polypeptides which form a tight triple helix. The collagen polypeptides are characterized by a long mid-section having the repeating sequence —Gly—X—Y—, where X and Y are often proline or hydroxyproline, bounded at each end by the "telopeptide" regions, which constitute less than about 5% of the molecule. The telopeptide regions of the collagen chains are typically responsible for the crosslinking between chains and for the immunogenicity of the protein. Collagen occurs in several "types" having differing physical properties. The most abundant types are Types I–III. Collagen is typically isolated from natural sources, such as bovine hide, cartilage, or bones. Bones are usually dried, defatted, crushed, and demineralized to extract collagen, while hide and cartilage are usually minced and digested with proteolytic enzymes (other than collagenase). As collagen is resistant to most proteolytic enzymes, this procedure conveniently serves to remove most of the contaminating protein found with collagen.

Collagens suitable for use in the present invention include all types of collagen, preferably types I, III, and IV. Collagens may be soluble (for example, commercially available Vitrogen® 100 collagen-in-solution), and may have or omit the telopeptide regions. Preferably, the collagen will be reconstituted fibrillar atelopeptide collagen, for example, Zyderm® I Collagen Implant (ZCI), Zyderm II Collagen Implant, Zyplast® Collagen Implant, or atelopeptide collagen-in-solution (CIS; available from Celtfix Pharmaceuticals, Santa Clara, Calif., under the trademark Vitrogen 100 collagen-in-solution). Various forms of collagen are available commercially, or may be prepared by the processes described in, for example, U.S. Pat. Nos. 3,949,073; 4,424,208; 4,488,911; 4,557,764; 4,582,640; 4,642,117; 4,689,399; 4,725,671; 5,024,841; 5,110,604; 5,162,430; 5,324,775; and 5,328,955, all of which are incorporated herein by reference.

The choice of substrate-reactive, substrate non-reactive, substrate-selective, tissue-reactive, tissue non-reactive, and tissue-selective functional groups will depend on the substrate material used and the receptive tissue in need of treatment.

For example, collagen lacks the amino acid cysteine, whereas cysteine is a common amino acid found in most animal tissues. By selecting a hetero-bifunctional binding agent which has at least one cysteine-selective functional group and at least one substrate-reactive (in this case, collagen-reactive) functional group, an anti-adhesion binding agent may be formulated which will react preferentially to covalently bind the substrate (in this case, collagen) to the receptive tissue (in this case, the cysteine groups found in the receptive tissue).

Of course, if the collagen-reactive functional group is also a tissue-reactive group, it may (depending on the reaction kinetics) be necessary to permit the anti-adhesion binding agent to react with the collagen substrate material (either partially or completely) prior to permitting reaction with the receptive tissue. Alternatively, if an anti-adhesion binding agent having both substrate-selective and tissue-selective functional groups, such sequential reaction steps may not be necessary.

It is preferred that functional groups intended to be reactive with receptive tissue, to covalently bond to the tissue to form the anti-adhesion device, are not substantially water-sensitive. That is, such preferred functional groups do not tend to react chemically with adventitious water, such as that found in or around the receptive tissue, thereby becoming unavailable to react with the receptive tissue to form the covalently bonded anti-adhesion device. For groups which are partially water-sensitive, additional factors, such as the number or proportion of such reactive functional groups, or their environment (as affected, for example, by a pH or salt buffer solution) may be controlled to reduce the relative reaction with adventitious water.

A wide variety of protein-reactive functional groups are known to those of skill in the art. Most of such protein-reactive functional groups are collagen-reactive and tissue-reactive functional groups. In particular, most functional groups which are generally reactive towards amino groups (—$NH_2$) (e.g., "amino-reactive groups") are also collagen-reactive and tissue-reactive.

Examples of preferred amino-reactive groups (which are also collagen-reactive and generally tissue-reactive functional groups) include:

active ester groups (—C(=O)OR*, wherein R* is an activating group, such as succinimidyl, 2,4-dinitrophenyl, or 1-hydroxybenzotriazol-2-yl) which react with amino groups to yield amide linkages (—NH—C(=O)—);

haloacetyl groups (—C(=O)$CH_2$X, where X is Cl, Br, or I) which react with amino groups to yield amine linkages (—NH—);

azide groups (—N=N+=N—) which react with many types of bonds such as C—H or C=C to form secondary amine linkages (—NH—) and liberate nitrogen ($N_2$);

haloformate groups (—OC(=O)X, where X is Cl, Br, or I) which react with amino groups to yield carbamate linkages (—NH—C(=O)O—);

sulfonyl halide groups (—$SO_2$X, wherein X is Cl, Br, or I) which react with amino groups to yield sulfonamide linkages (—S(=O)$_2$—NH—);

isocyanate groups (—NCO) which react with amino groups to yield urea linkages (—NH—(C=O)—NH—);

isothiocyanate groups (—NCS) which react with amino groups to yield thiourea linkages (—NH—(C=S)—NH—);

acid anhydride groups (—C(=O)OC(=O)R, wherein R is an organic group such as alkyl) which react with amino groups to yield amide linkages (—NH—C(=O)—);

acid halide groups (—C(=O)X, where X is Cl, Br, or I) to yield amide linkages (—NH—C(=O)—); and imidate ester groups (—C(=NR)OR, wherein R is an organic group such as alkyl) which react with amino groups to yield imidate linkages (—NH—C(=NR)—).

Examples of more preferred amino-reactive groups include active ester groups, haloacetyl groups, and azide groups. Still more preferred examples include active ester groups, and in particular, the succinimidyl ester group.

Examples of collagen non-reactive (and therefore tissue-selective) functional groups include functional groups which are reactive towards sulfhydryl groups (—SH) or disulfide groups (—SS—), but are essentially unreactive towards amino groups (—$NH_2$), herein referred to as "sulfhydryl-selective functional groups". A number of such groups are discussed below.

(i) Disulfide groups (—S—S—R), wherein R is a group such as 2-pyridinyl. Such groups may easily be prepared by one of skill in the art; one useful method involves derivatization of a sulfhydryl group (—SH) with 2,2'-dipyridyl disulfide. Disulfide groups (—S—S—R) react with the sulfhydryl groups (—SH) of compounds found in receptive tissue (e.g., tissue—SH) to form a disulfide linkage (e.g., —S—S-tissue), while such disulfide groups are essentially unreactive towards amino groups (—$NH_2$) such as those found in collagen. Examples of preferred disulfide groups include 2-pyridinyl-disulfide group and the 3-(carboxylic acid)-4-nitro-phenyl-disulfide group.

(ii) Haloacetyl groups (—C(=O)$CH_2$X), wherein X is a chloro, bromo, or iodo group, and most preferably chloro. Such groups may easily be prepared by one of skill in the art; several useful methods include reaction of an alpha-hydroxyl carbonyl (—C(=O)—$CH_2$OH) with a haloacid (e.g., HCl, HBr, HI), a halophosphine (e.g., $PCl_5$, $PBr_3$, $PI_3$), or with $SOCl_2$. Haloacetyl groups are reactive both with sulfhydryl groups (—SH) and amino groups (—$NH_2$). However, the chloroacetyl group (X=Cl) is much more reactive towards sulfhydryl groups (e.g., such as those found in receptive tissue) than towards amino groups. Thus, the chloroacetyl group is effectively collagen-non-reactive or tissue-selective, and reacts with sulfhydryl groups (—SH) of compounds found in receptive tissue to yield sulfide linkage (e.g., —C(=O)$CH_2$—S-tissue).

(iii) Methyl ester groups (—C(=O)$OCH_3$); halomethyl ester groups (—C(=O)$OCH_2$X), wherein X is a chloro, bromo, or iodo group, preferably a chloro group; and dihalomethyl ester groups (—C(=O)OCH$X_2$), wherein each X is independently a chloro, bromo, or iodo group, preferably both X's are chloro groups. Such groups may easily be prepared by one of skill in the art; one useful method involves derivatization of an acid halide with the appropriate halomethanol. Although methyl ester, halomethyl ester, and dihalomethyl ester groups react with sulfhydryl (—SH) groups as well as amino (—$NH_2$) groups and water ($H_2O$), these groups react much more rapidly with sulfhydryl groups (—SH), such as those of compounds found in receptive tissues (e.g., tissue—SH) to form a thioamide linkage (e.g., —C(=O)—S-tissue). Preferred esters are the halomethyl esters, more preferably chloromethyl esters.

(iv) β-Nitrovinyl groups (—CH=CHNO$_2$). Such groups may easily be prepared by one of skill in the art; one useful method involves derivatization of an alcohol with an appropriate halogenated nitrovinyl compound (for example, I—$CH_2$—CH=CHNO$_2$). Although β-Nitrovinyl groups react with both sulfhydryl groups (—SH) and amino groups (—$NH_2$), they are more reactive towards sulfhydryl groups (—SH), such as those of compounds found in receptive tissue (e.g., tissue—SH) to form a sulfide linkage (e.g., —CH(—S-tissue)$CH_2NO_2$).

In addition, functional groups may be chosen which are both substrate-reactive and tissue-reactive, but for which, under specified conditions, reaction with functional groups of the substrate proceeds much more slowly than reaction with functional groups of compounds found in the receptive tissue. Under such conditions, these functional groups may be considered collagen non-reactive and, therefore, tissue-selective. Several examples of such groups are discussed below.

(v) N-hydroxy succinimidyl esters (—C(=O)O—N[—C(=O)CH$_2$CH$_2$C(=O)—]) react more quickly with sulfhydryl groups (—SH), yielding a thioester linkage (—S—C(=O)—), than with amine groups (—NH$_2$), yielding an amide linkage (—NH—C(=O)—) when the pH is approximately neutral. Such N-hydroxy succinimidyl ester groups may easily be prepared by one of skill in the art; one useful method involves derivatization of a carboxylic acid with NHS (N-hydroxysuccinimide) and EDC (1-ethyl-3-(3-dimethylaminopropyl)carbodiimide hydrochloride; (CH$_3$)$_2$NCH$_2$CH$_2$CH$_2$N=C=NCH$_2$CH$_3$).

(vi) Maleimidyl groups (—N[—C(=O)—CH=CH—C(=O)—]) react much more quickly with sulfhydryl groups (—SH), yielding a sulfide linkage (—S—), than with amine groups (—NH$_2$), yielding a secondary amine linkage (—NH—) when the pH is approximately neutral. Such maleimidyl groups may easily be prepared by one of skill in the art; one useful method involves derivatization of an amino group with maleic anhydride.

One preferred class of anti-adhesion binding agents which are particularly useful in combination with substrate materials comprising collagen have at least one collagen nonreactive group. Thus, one class of preferred anti-adhesion binding agents have at least one functional group which is:

(i) a disulfide group;

(ii) a haloacetyl group;

(iii) a halomethyl ester group;

(iv) a β-Nitrovinyl group;

(v) an N-hydroxy succinimidyl ester group; or (vi) a maleimidyl group.

More preferred anti-adhesion binding agents have at least one functional group which is:

(i) a disulfide group;

(ii) a haloacetyl group;

(iii) a halomethyl ester group; or (iv) a β-Nitrovinyl group;

Preferred anti-adhesion binding agents have at least one functional group which is a disulfide group, such as a 2-pyridinyl-disulfide group or a 3-(carboxylic acid)-4-nitrophenyl-disulfide group.

A number of compounds suitable for use as anti-adhesion binding agents are commercially available; several of these are identified in the examples below. These include Sulfo-LC-SPDP, Sulfo-LC-SMPT, SPDP, Sulfo-SIAB, Sulfo-SMCC, DNPNVB, ASIB, and APDP.

In addition, other suitable anti-adhesion binding agents may be synthesized using known methods. A preferred class of anti-adhesion binding agents are those derived from polymeric compounds such as polyethylene glycol ("PEG"; HO(CH$_2$CH$_2$O)$_n$H) wherein n is between 10 and about 500 (molecular weight about 400 to about 22,000), more preferably between about 20 and about 200 (molecular weight about 900 to about 9,000). The terminal hydroxyl (—OH) groups of PEG may be derivatized to yield hetero-bifunctional binding agents suitable for use as anti-adhesion binding agents. A number of such derivatives are presented in the Examples below. For example, one hydroxy terminus may be derivatized to yield a succinimidyl active ester, and the other hydroxy terminus may be derivatized to yield a 2-pyridinyl-disulfide. Such PEG-derived binding agents are preferred in view of the favorable chemical and physical properties, such as low toxicity, low immunogenicity, biocompatible breakdown products, and the like, which have been shown in the art. See, for example, U.S. Pat. No. 5,162,430 to Rhee et al.

The anti-adhesion compositions and films of the present invention may further comprise optional active agents for improved efficacy. Such active agents include anti-fibrotics (for example, fibrinolysin, papain, streptokinase, tissue plasminogen activator, urokinase, hyaluronidase, chymotrypsin, trypsin, and pepsin), anti-coagulants (for example, heparin, citrates, and oxalates), anti-inflammatory agents (for example, corticosteroid, ibuprofren, antihistamines), antibiotics (for example, tetracyclines and cephalosporins), growth factors (for example, IGF-I, TGF-II, EGF, FGF, TGF-α, and TGF-β), and hormones and growth-regulating agents (for example, insulin, somatotropin, and interferon). These active agents may simply be mixed with other components of the anti-adhesion compositions or films, or may be covalently bonded to other components therein, such as, for example, the substrate material, using methods known in the art. The relative quantity of active agents (e.g., the dosage) will depend upon factors such as the patient's age, weight, and health, the indication, and the desired effect.

The anti-adhesion compositions and films of the present invention may also further comprise optional inactive agents which may be included for reasons of improved physical properties (such as strength, flexibility, ease of handling, and the like). Such inactive agents include, for example, glycerol, heavy molecular weight poly-ox (Union Carbide, molecular weight approximately $5\times10^3$ to $7\times10^6$), and carbohydrates.

Films useful in the device of the present invention for the prevention of the formation of adhesions must possess a number of characteristics. The anti-adhesion films of the present invention, and the components thereof, are best chosen to be biocompatible. The term "biocompatible" as used herein relates to components which, when administered in a desired manner, do not induce significant adverse effects, such as substantial immunological, inflammatory, or necrotic response.

The anti-adhesion films of the present invention have a film thickness large enough and pore size small enough to permit the film to act as a physical barrier, specifically, to prevent or impede the free flow of tissue fluids and their components across the film. If appropriate, the pore size of a membrane component of the anti-adhesion film may be particularly chosen to optimize the film's action as a physical barrier.

The anti-adhesion films of the present invention are strong and flexible, particularly in the directions of the plane of the film, so as to permit reasonably unrestricted movement (including, for example, contraction of vasculature and musculature, movement over and against adjacent tissues) without tearing, ripping, or otherwise compromising the film's integrity as a physical barrier. Properties such as film strength, flexibility, and texture may be varied by controlling the properties of the substrate material. For example, for membranes formed from fibrous materials such as collagen, the fiber size and shape and the degree of crosslinking is known to influence the strength, flexibility, and texture of membranes formed therefrom; these parameters may be adjusted by one of skill in the art to optimize the film's physical properties.

As opposed to the non-resorbable membranes known in the prior art, the anti-adhesion membranes of the present invention are slowly bioresorbable. The resorptivity of an anti-adhesion film is reflected in its bioabsorption period.

The term "bioabsorption period" as used herein relates to the period of time after which substantial bioabsorption of the substrate material has occurred, and the remnants of the anti-adhesion film no longer effectively function as a physical barrier. At some time after the bioabsorption period, the original components of the anti-adhesion film are completely or nearly completely resorbed, leaving little or no residue. Exemplary bioabsorption periods will depend on the indication and application site, and may vary between 10 and 90 days, more preferably between 20 and 60 days, still more preferably between 30 and 50 days.

The anti-adhesion devices of the present invention may be prepared using a variety of methods. For example, an anti-adhesion composition comprising substrate material and anti-adhesion binding agent may be applied to the receptive tissue. Chemical reaction between the substrate material and the anti-adhesion binding agent may be incomplete, partially complete, or fully complete prior to applying the anti-adhesion composition to the receptive tissue. A low viscosity liquid-form anti-adhesion composition may be applied, for example, by painting, spraying, or injecting. A high viscosity gel-form anti-adhesion composition may be applied by pouring, smearing, or injecting. The anti-adhesion composition may then be permitted to "cure" for a time to form the anti-adhesion film and, simultaneously, the anti-adhesion device.

The term "curing" as used herein refers to both the formation of a coherent film from the anti-adhesion composition and to the reaction of functional groups of the anti-adhesion composition with functional groups of compounds found in the receptive tissue, thereby forming the anti-adhesion device. Curing may be initiated, augmented, or terminated by controlling physical and chemical conditions, such as, for example, pH, temperature, availability of adventitious water, as well as by exposure to radiation, for example, to activate or deactivate (e.g., quench) functional groups. The "curing" time may vary according to the particular anti-adhesion composition used and the required or desired degree of covalent bonding between the anti-adhesion composition and the receptive tissue, and may be limited by the constraints of the surgery.

The term "apply" as used herein is generic to methods of applying, attaching, implanting, injecting, and the like, and combinations thereof. Methods of applying include, for example, pouring, painting, smearing, injecting, and spraying. If the anti-adhesion composition is in liquid form, preferred methods include painting, injecting, and spraying. If the anti-adhesion composition is in gel form, preferred methods include pouring, smearing, and injecting. If the anti-adhesion composition is semi-solid or solid (such as a membrane), preferred methods of application include draping and taping (for example, with biomedical adhesive tape using fibrin glue); suturing (for example, with microsutures) can be used, but preferred methods do not involve suturing and most preferred methods further do not involve taping.

Alternatively, anti-adhesion devices may be prepared by pre-coating one side of a preformed substrate material membrane with a composition comprising an anti-adhesion binding agent, and subsequently applying the pre-coated membrane to the receptive tissue. The pre-coated membrane may be applied immediately after pre-coating, or the anti-adhesion binding agent may be permitted to react (either partially or completely) with the substrate material of the membrane prior to application to the receptive tissue.

By yet another method, anti-adhesion devices may be prepared by pre-coating the receptive tissue with a composition comprising an anti-adhesion binding agent (for example, by painting or spraying), and subsequently applying a pre-formed substrate material membrane to the pre-coated receptive tissue. Again, the membrane may be applied immediately after pre-coating the receptive tissue, or the anti-adhesion binding agent may be permitted to react (either partially or completely) with the receptive tissue prior to application of the membrane.

By still another method, anti-adhesion devices may be formed by pre-coating the receptive tissue with a composition comprising an anti-adhesion binding agent (for example, by painting or spraying), and subsequently applying a gel-form composition comprising substrate material membrane to the pre-coated receptive tissue. Similarly, anti-adhesion films may be formed by pre-coating the receptive tissue with a composition comprising an anti-adhesion binding agent (for example, by painting or spraying), and subsequently applying a liquid-form composition comprising substrate material membrane to the pre-coated receptive tissue (also by, for example, painting or spraying). Again, the anti-adhesion binding agent may be permitted to react (either partially or completely) before applying the substrate material.

By yet another method, anti-adhesion devices may be formed using an anti-adhesion composition wherein the functional groups intended to react with, and thereby covalently bond to, the receptive tissue, are photoactivated. A low-viscosity anti-adhesion composition may be applied, for example, by painting or spraying. A portion of the patient, and particularly, that portion in need of treatment, may then be appropriately irradiated to activate the anti-adhesion composition and thereby permit curing. Indeed, for those anti-adhesion compositions comprising substrate materials which may be crosslinked by irradiation, such as collagen, this method of inducing curing may also serve to improve the mechanical properties of the anti-adhesion film.

The substrate material may itself be chemically modified. For example, many substrate materials may be chemically crosslinked to provide desired physical properties, for example, shape, strength, elasticity, biological stability, and the like. In particular, for substrate materials comprising collagen, collagen molecules may be crosslinked to each other or to other substrate molecules. Such crosslinking may be achieved by reaction with crosslinking agents or exposure to radiation. Examples of crosslinking agents include aldehydes such as glutaraldehyde and formaldehyde, divinyl sulfone, epoxides, carbodiimides, and imidazoles. Additional cross-linking agents include polymeric crosslinking agents such as multifunctionally activated polyethylene glycols, for example, disuccinimidyl poly(ethylene glycol) glutarate, as described in U.S. Pat. Nos. 5,162,430; 5,324,775; 5,328,955; 5,292,802; and 5,308,889. See also U.S. Pat. No. 4,179,337 issued to Davis for additional linking groups.

As an alternative to, or in addition to, chemical modification, the substrate material may be physically modified, yielding, for example, low viscosity liquids, gels, pastes, sponges (for example, by lyophilization), or membranes (for example, by crosslinking).

The anti-adhesion compositions and devices of the present invention may be used in a wide variety of indications for the prevention of the formation of undesired adhesions (in particular, surgical adhesions) between tissues. The terms "prevent" and "prevention" as used herein in the context of adhesions are intended to include the complete prevention of the formation of any detectable adhesion, as well as the reduction in the adhesion formed, as measured by, for example, the quantity or severity of the adhesion.

Similarly, the terms "treat" and "treatment" as used herein refer particularly to the prevention of the formation of adhesions.

The anti-adhesion devices of the present invention may be applied using a variety of methods for a variety of indications. For example, in thoracic surgery, a low-viscosity anti-adhesion composition may be sprayed onto the surfaces to be treated, for example, onto the surfaces of organs which are near to or in contact with tissue which has been traumatized by surgery. In this manner, the various surfaces of the peritoneal lining may be sprayed, the anti-adhesion film permitted to "cure", and the surgery continued or completed. In this way, the anti-adhesion film prevents the formation of an adhesion between the peritoneal lining and adjacent tissues.

In another example, in abdominal surgery, a collagenous membrane may be painted with an appropriate anti-adhesion binding agent, permitted to react for a specified period of time, and subsequently wrapped around or draped over a portion of the small intestine which has been traumatized by surgery. In this way, the anti-adhesion film prevents the formation of an adhesion between the surgery site and adjacent and overlying portions of the small intestine or other organs.

In yet another example, ligament or tendon tissue may similarly be wrapped with a substrate material membrane which has been previously painted with an appropriate anti-adhesion binding agent, thereby preventing the formation of an adhesion between the tendon or ligament and the overlying skin or surface tissues.

In still another example, a gel-form anti-adhesion composition may be smeared or injected between the small bones, such as those of the fingers or toes, for example, during reconstructive surgery, thereby preventing restricted mobility resulting from the formation of an adhesion between the distinct bones.

In some instances it may be necessary to modify the receptive tissue to which the substrate material is to be attached, to render the receptive tissue more reactive or to create reactive sites on the tissue. For example, when it is desired to have —SH groups present on the tissue surface and the available functional groups on such tissue surface are disulfide groups, it is possible to reduce these disulfide (—S—S—) groups to sulfhydryl (—SH) groups using a reducing agent. Examples of such reducing agents include dithiothreitol (Cleland's reagent) and 2-mercaptoethanol, which is a very mild reducing agent. Such reducing agents can be applied directly to the tissue to be converted to reactive tissue prior to application of the anti-adhesion composition of the present invention.

An alternative method of rendering receptive tissue more reactive is to convert primary amino groups on the surface of such receptive tissue to sulfhydryl (—SH) groups. For example, Traut's Reagent (2-iminothiolane HCl) is known to be a protein modification reagent capable of reacting with primary amines to introduce sulfhydryl groups.

The reducing agents and Traut's Reagent described above can be applied to the receptive tissue in the same manner as described for the liquid form of the anti-adhesion composition of the present invention. In addition, when it is possible to render the receptive tissue more reactive using a gaseous reagent (a combination of compressed gas with one of the reagents described above), this is particularly advantageous, as the surgeon can "blow" the tissue surface clear of potentially interfering fluid materials, while simultaneously making the tissue more reactive.

EXAMPLES

The following examples are put forth so as to provide those of ordinary skill in the art with an enabling disclosure and description of how to make the anti-adhesion compositions and devices of the present invention, and are not intended to limit the scope of what the inventors regard as their invention. The present invention is shown and described herein at what are considered to be the most practical and preferred embodiments. It is recognized, however, that departures may be made therefrom which are within the scope of the invention, and that obvious modifications will occur to one skilled in the art upon reading this disclosure.

Example 1

Use of an Anti-Adhesion Binding Agent With "Disulfide" and "Succinimidvl" Groups: Sulfo-LC-SPDP A flow chart which illustrates the preparation and use of an anti-adhesion binding composition comprising the titled anti-adhesion binding agent is shown in FIG. 1. Sulfo-LC-SPDP (sulfosuccinimidyl-6-[3-(2-pyridyldithio) propionamido]hexanoate, sodium salt, Compound 1) is first reacted with collagen. The sulfosuccinimidyl group of the Sulfo-LC-SPDP, acting as a collagen-reactive functional group, reacts with free amino groups (—NH$_2$) of collagen, such as those of lysine amino acid residues or at the N-terminals, to form an amide linkage, at an approximate pH of 7.0, for example, in phosphate buffer yielding Compound 2. The by-product, N-hydroxysuccinimide, is nominally non-toxic, and may be removed, for example, by washing, if desired. This anti-adhesion composition, Compound 2, is then reacted with receptive tissue. The 2-pyridinyldithio group of the Sulfo-LC-SPDP moiety (e.g., possessing a disulfide linkage), acting as a tissue-selective group, reacts with free sulfhydryl groups (—SH) found in compounds of receptive tissue (for example, fibrin or other sulfhydryl-containing tissue macromolecule) to form a covalent disulfide linkage (—S—S—) to the tissue compounds. Again, the by-product, pyridine-2-thione is nominally non-toxic.

Analogous results may be obtained with Sulfo-LC-SMPT (sulfosuccinimidyl-6-[alphamethyl-alpha-(2-pyridyldithio)toluamido]hexanoate, sodium salt, Compound 3) or SPDP (N-succinimidyl-3-(2-pyridinyldithio)propionate, Compound 4).

Example 2

Figure 2:
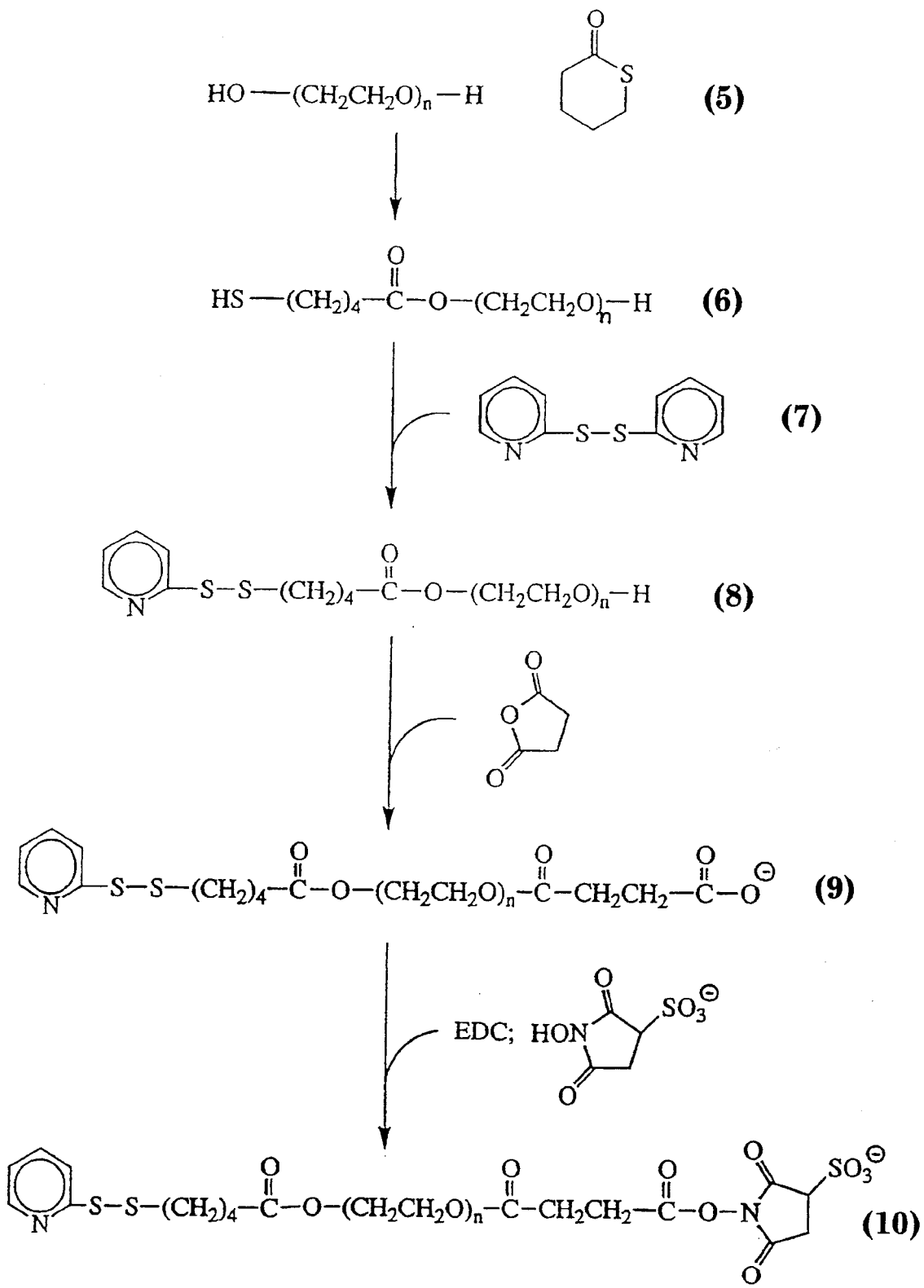
FIG. 2 is a flow chart which illustrates a synthetic route for the preparation of a PEG-derived anti-adhesion binding agent with sulfosuccinimidyl and disulfide groups.

Anti-Adhesion Binding Agent With "Disulfide" and "SuccinimidVl" Groups Derived From PEG A flow chart which illustrates a route for the synthesis of this anti-adhesion binding agent is shown in FIG. 2. One equivalent of polyethylene glycol (PEG, molecular weight about 3,000) is combined with 1 equivalent of 1-thia-1,2-pyrone, Compound 5, and heated and stirred under acid conditions to yield Compound 6. Depending on the conditions of reaction, it may be necessary to protect one of the —OH end groups on Compound 5 so that Compound 6 is produced. Techniques for protection of such an end group are known in the art and are not specified herein.

The intermediate Compound 6 is then reacted with 1.2 equivalents of 2,2'-dipyridyl disulfide, Compound 7, to yield the disulfide intermediate, Compound 8. The intermediate Compound 8 is then reacted with 1.2 equivalents of succinic anhydride to yield the succinate intermediate, Compound 9. The intermediate Compound 9 is then reacted with 3 equivalents of 1-ethyl-3-(3-dimethylaminopropyl)carbodiimide hydrochloride("EDC";

$(CH_3)_2NCH_2CH_2CH_2N=C=NCH_2CH_3)$ and 1.2 equivalents of sulfo-N-hydroxysuccinimide, added dropwise, to yield a mixture of compounds, including PEG, monofunctionalized PEGs, homobifunctionalized PEGs, and heterobifunctionalized PEGs. The heterobifunctionalized PEG of interest (e.g., the anti-adhesion binding agent, Compound 10) may then be separated, isolated, and purified using, for example, high pressure liquid chromatography (HPLC) with a non-aqueous mobile phase.

Figure 3:
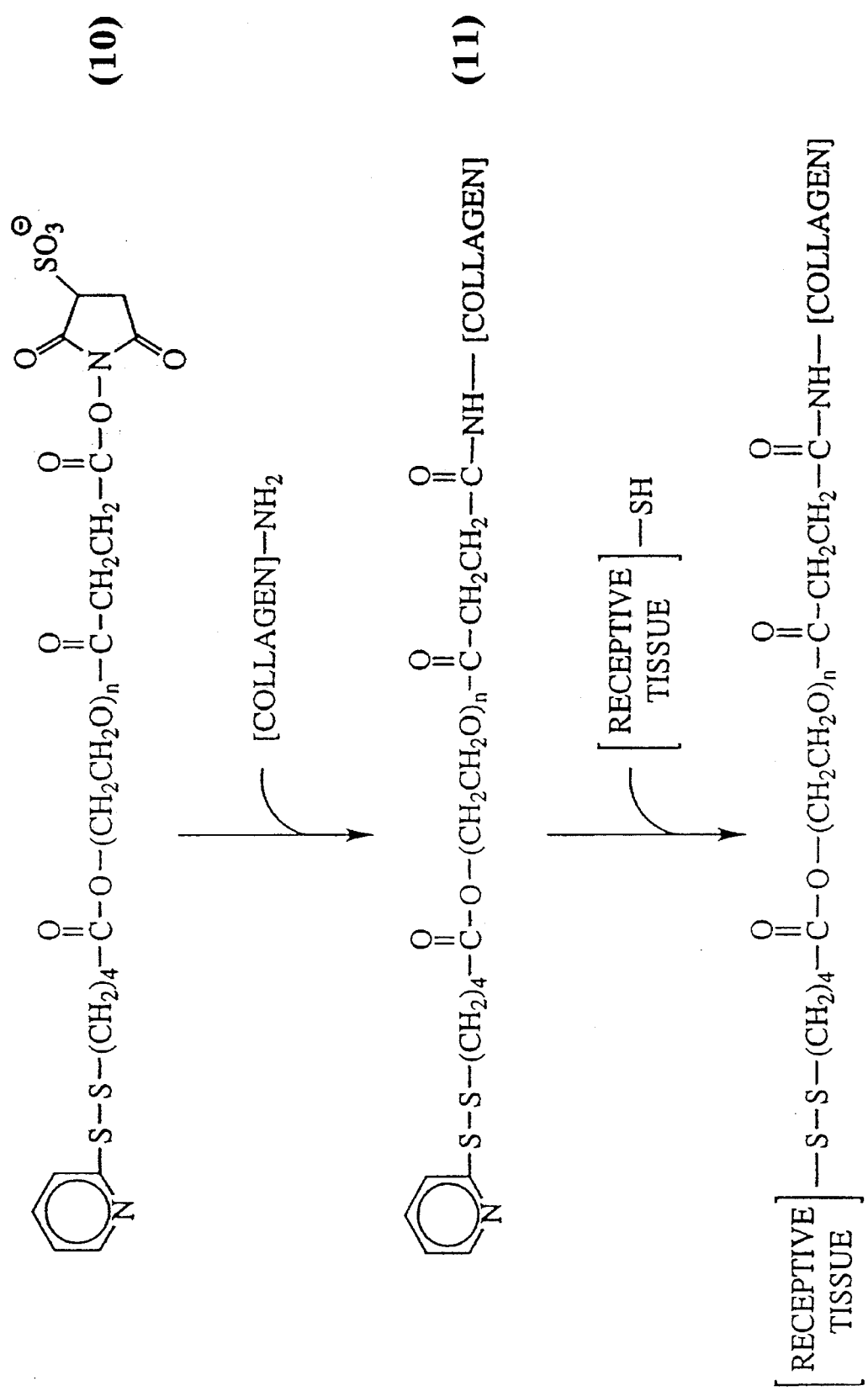
FIG. 3 is a flow chart which illustrates the preparation and use of an anti-adhesion composition comprising collagen and the PEG-derived anti-adhesion binding agent shown in FIG. 2.

A flow chart which illustrates the preparation and use of an anti-adhesion binding composition comprising the anti-adhesion binding agent, Compound 10, in a manner analogous to that of Example 1, is shown in FIG. 3. The anti-adhesion binding agent, Compound 10, is first reacted with collagen to yield the anti-adhesion binding composition, Compound 11, which is subsequently reacted with receptive tissue to yield the anti-adhesion film.

Example 3

Figure 4:
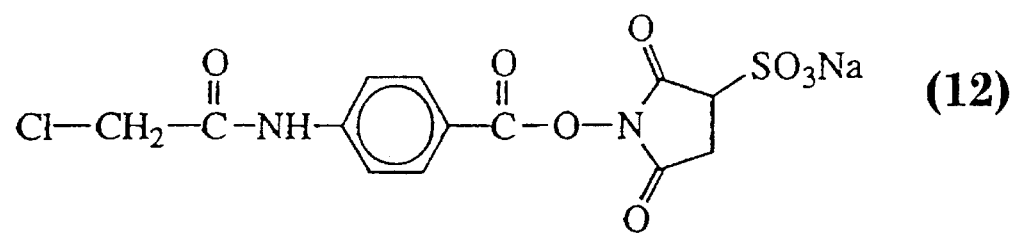
FIG. 4 is a flow chart which illustrates the preparation and use of an anti-adhesion composition comprising collagen and the anti-adhesion binding agent Sulfo-SCAB.
Figure 4:
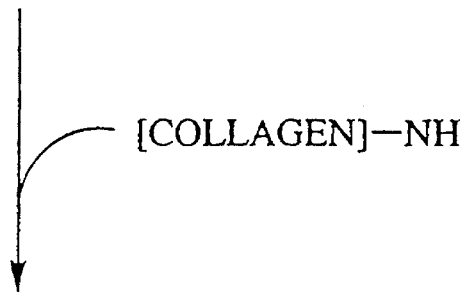
Figure 4:
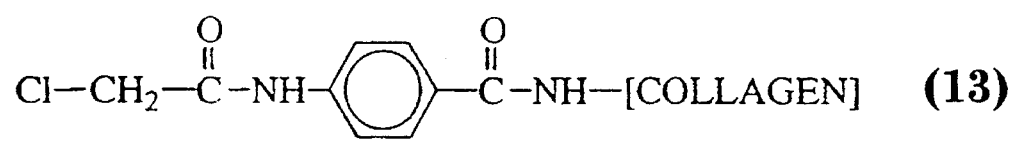
Figure 4:
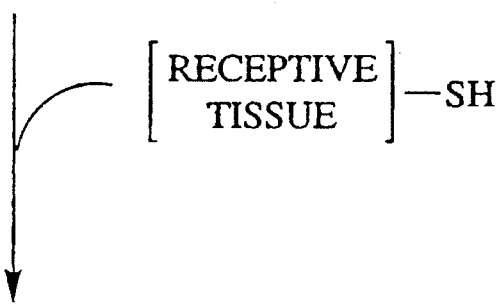
Figure 4:
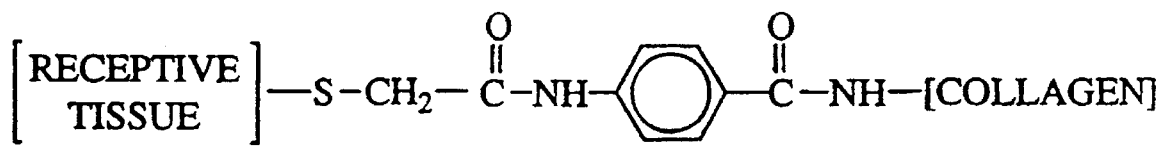

Use of an Anti-Adhesion Binding Agent With "Haloacetyl" and "SuccinimidVl" Groups: Sulfo-SCAB A flow chart which illustrates the preparation and use of an anti-adhesion binding composition comprising the titled anti-adhesion binding agent is shown in FIG. 4. Sulfo-SCAB (sulfosuccinimidyl-(4-chloroiodoacetyl)aminobenzoate, sodium salt, Compound 12) is first reacted with collagen. The sulfosuccinimidyl group of the Sulfo-SCAB, acting as a collagen-reactive functional group, reacts with free amino groups ($-NH_2$) of collagen, such as those of lysine amino acid residues or at the N-terminals, to form an amide linkage, at an approximate pH of 7.0, for example, in phosphate buffer, yielding the anti-adhesion composition, Compound 13. The by-product, N-hydroxysuccinimide, is nominally non-toxic, and may be removed, for example, by washing, if desired. This anti-adhesion composition is then reacted with receptive tissue. The haloacetyl group of the Sulfo-SCAB moiety (e.g., possessing a haloacetyl group), acting as a tissue-selective group, reacts with free sulfhydryl groups (—SH) found in compounds of receptive tissue (for example, fibrin or other sulfhydryl-containing tissue macromolecule) at pH 6.5 to 7.5 to form a covalent sulfide linkage (—S—) to the tissue compounds. Again, the by-product, halide ion, is nominally non-toxic.

Other haloacetyl groups may be used as tissue-selective groups, such as bromoacetyl and chloroacetyl. The reactivity of haloacetyl groups towards sulfhydryl groups (such as those found in receptive tissue compounds) increases with increasing halogen atomic number; that is, iodoacetyl is more reactive than bromoacetyl, which is more reactive than chloroacetyl. In contrast, selectivity of haloacetyl groups towards reaction with sulfhydryl groups decreases with increasing atomic number; that is, chloroacetyl is more sulfhydryl-selective than bromoacetyl, which is more sulfhydryl-selective than iodoacetyl. Thus, chloroacetyl is preferred as a sulfhydryl-selective group. In addition, dihaloacetyl and trihaloacetyl groups may be used as tissue-selective groups.

Example 4

Figure 5:
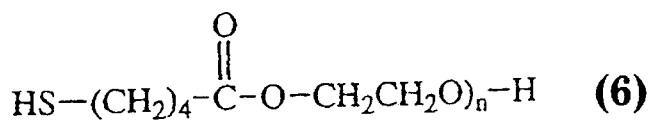
FIG. 5 is a flow chart which illustrates a synthetic route for the preparation of a PEG-derived anti-adhesion binding agent having haloacetyl and disulfide groups.
Figure 5:
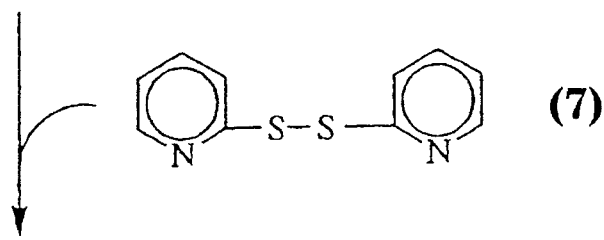
Figure 5:
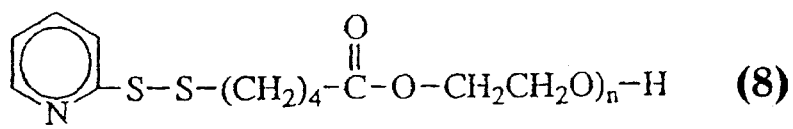
Figure 5:
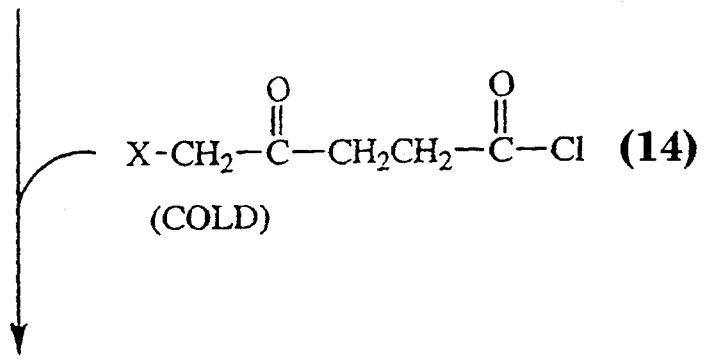
Figure 5:
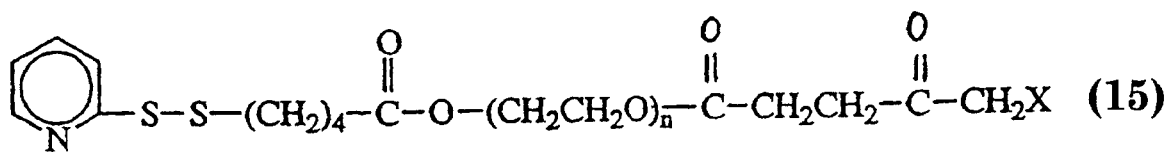

Anti-Adhesion Binding Agent With "Haloacetyl" and "Disulfide" Groups Derived From PEG A flow chart which illustrates the preparation and use of an anti-adhesion binding composition comprising the titled anti-adhesion binding agent is shown in FIG. 5. Compound 6, previously described, is then reacted with 1.2 equivalents of 2,2'-dipyridyl disulfide, Compound 7, to yield the disulfide intermediate, Compound 8. The intermediate Compound 8 is then reacted with an iodoacetyl acid chloride compound, such as $CH_2X-C(=O)-CH_2CH_2-C(=O)Cl$ (Compound 14) to yield a mixture of compounds including the heterobifunctionalized PEG of interest, Compound 15, which may then be separated, isolated, and purified using, for example, high pressure liquid chromatography (HPLC) with a non-aqueous mobile phase.

Figure 6:
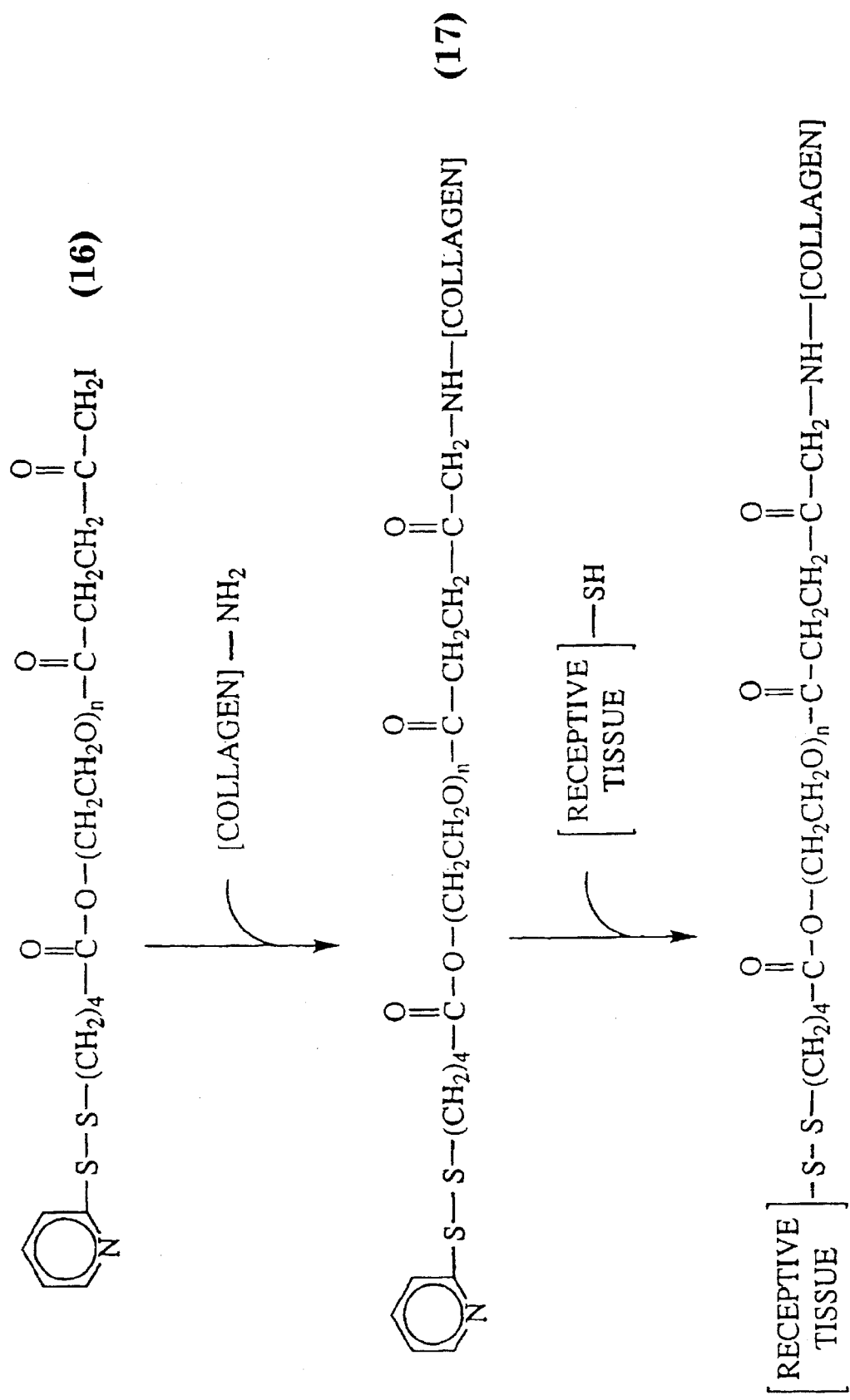
FIG. 6 is a flow chart which illustrates the preparation and use of an anti-adhesion composition comprising collagen and the PEG-derived anti-adhesion binding agent shown in FIG. 5.

A flow chart which illustrates the preparation and use of an anti-adhesion binding composition comprising the anti-adhesion binding agent, Compound 15, in the form of iodoacetyl, is shown in FIG. 6. An anti-adhesion binding agent, Compound 16, is first reacted with collagen to yield the anti-adhesion binding composition, Compound 17, which is subsequently reacted with receptive tissue to yield the anti-adhesion film.

Example 5

Figure 7:
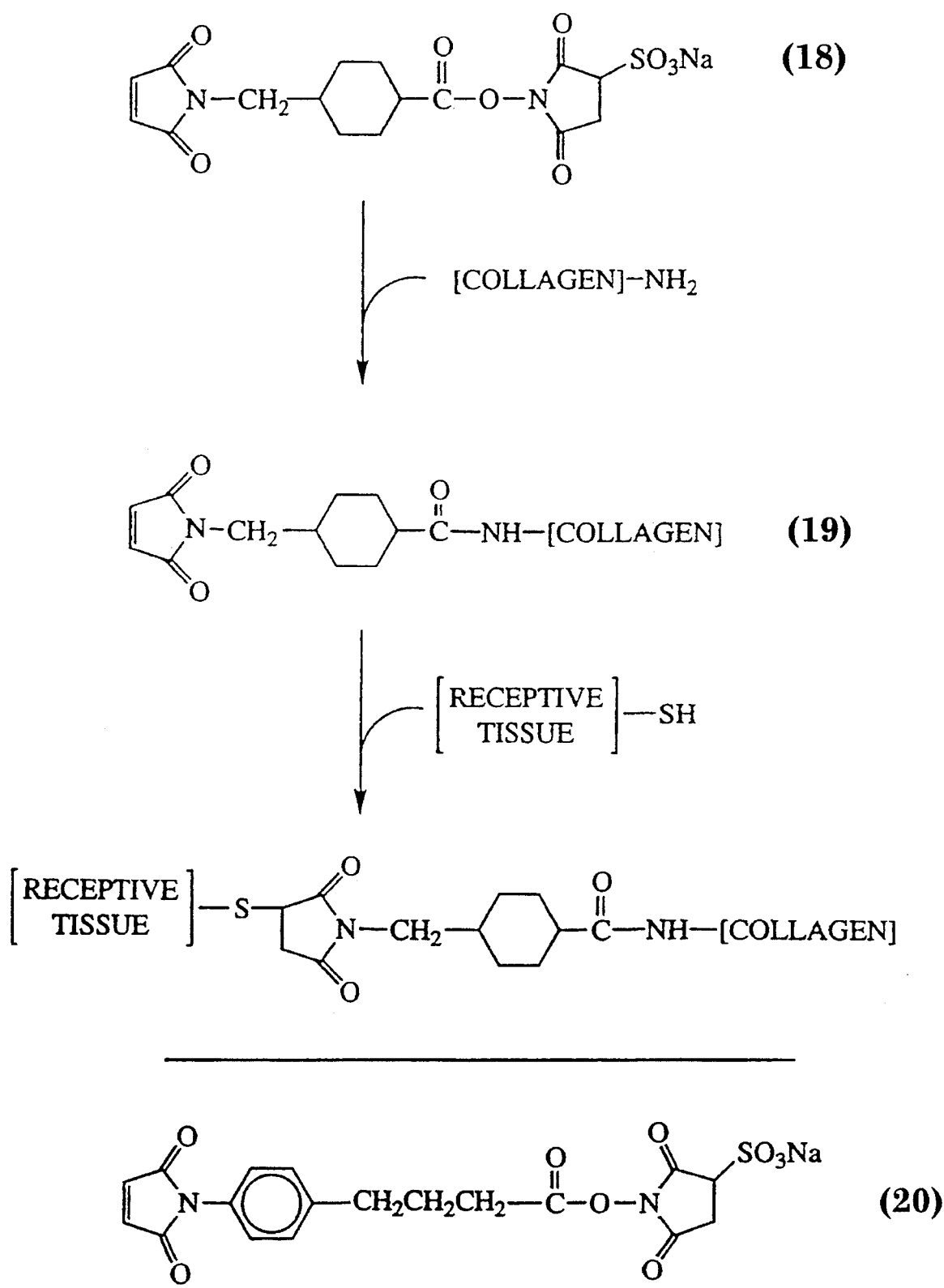
FIG. 7 is a flow chart which illustrates the preparation and use of an anti-adhesion composition comprising collagen and the anti-adhesion binding agent Sulfo-SMCC, and the analogous compound Sulfo-SMPB.

Use of an Anti-Adhesion Binding Agent With "Maleimidyl" and "Succinimidyl" Groups: Sulfo-SMCC A flow chart which illustrates the preparation and use of an anti-adhesion binding composition comprising the titled anti-adhesion binding agent is shown in FIG. 7. Sulfo-SMCC (sulfosuccinimidyl-(4-(N-maleimidomethyl) cyclohexane-1-carboxylate, sodium salt, Compound 18) is first reacted with collagen. The sulfosuccinimidyl group of the Sulfo-SMCC, acting as a collagen-reactive functional group, reacts with free amino groups ($-NH_2$) of collagen, such as those of lysine amino acid residues or at the N-terminals, to form an amide linkage, at an approximate pH of 7.0, for example, in phosphate buffer, yielding the anti-adhesion composition, Compound 19. The by-product, N-hydroxysuccinimide, is nominally non-toxic, and may be removed, for example, by washing, if desired. This anti-adhesion composition, Compound 19, is then reacted with receptive tissue. The maleimidyl group of the Sulfo-SMCC moiety (e.g., possessing an $\alpha,\beta$-unsaturated carbonyl group), acting as a tissue-selective group, reacts at the a-position with free sulfhydryl groups (—SH) found in compounds of receptive tissue (for example, fibrin or other sulfhydryl-containing tissue macromolecule) to form a covalent sulfide linkage (—S—) to the tissue compounds.

Analogous results may be obtained with Sulfo-SMPB (sulfo-succinimidyl-4-(pmaleimidophenyl)butyrate, Compound 20).

Example 6

Figure 8:
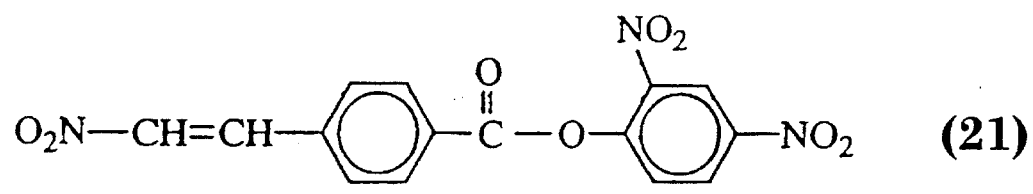
FIG. 8 is a flow chart which illustrates the preparation and use of an anti-adhesion composition comprising collagen and the anti-adhesion binding agent DNPNVB.
Figure 8:
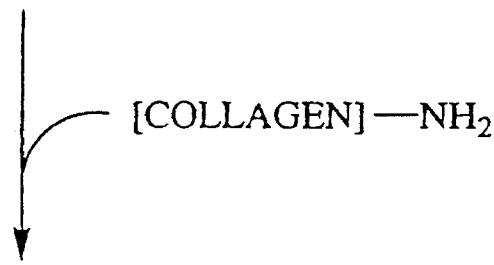
Figure 8:
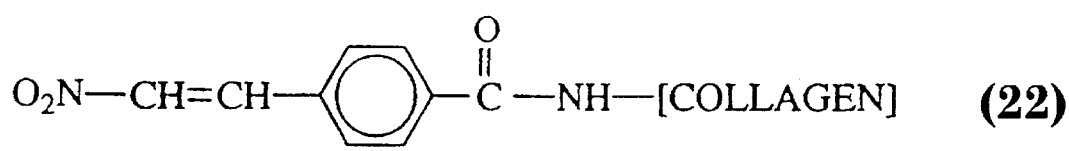
Figure 8:
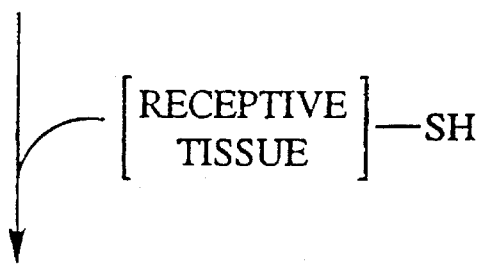
Figure 8:
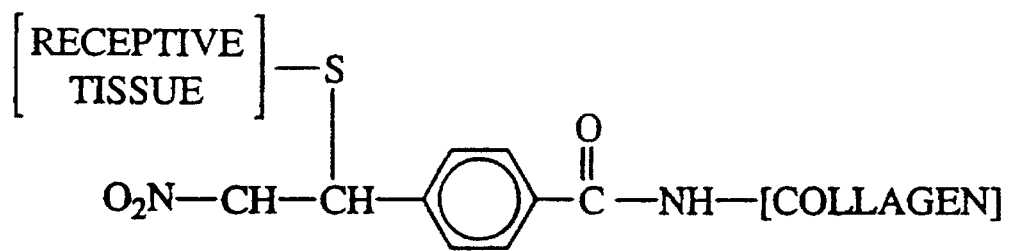

Use of an Anti-Adhesion Binding Agent With "Dinitrophenyl Ester" and "Nitrovinyl" Groups: DNPNVB A flow chart which illustrates the preparation and use of an anti-adhesion binding composition comprising the titled anti-adhesion binding agent is shown in FIG. 8. DNPNVB (2,4-dinitrophenyl-p-($\beta$-nitrovinyl) benzoate, Compound 21) is first reacted with collagen. The 2,4-dinitrophenoxy group of the DNPNVB, acting as a collagen-reactive functional group, reacts with free amino groups ($-NH_2$) of collagen, such as those of lysine amino acid residues or at the N-terminals, to form an amide linkage, at an approximate pH of 6.0 to 7.5, yielding the anti-adhesion composition, Compound 22. The by-product, 2,4-dinitrophenoxide, is nominally non-toxic, and may be removed, for example, by washing, if desired. This anti-adhesion composition, Compound 22, is then reacted with receptive tissue. The nitrovinyl group of the DNPNVB moiety (e.g., possessing an activated double bond), acting as a tissue-selective group, reacts at the carbon alpha to the nitro group with free sulfhydryl groups (—SH) found in compounds of receptive tissue (for example, fibrin or other sulfhydryl-containing tissue macromolecule) to form a covalent sulfide linkage (—S—) to the tissue compounds.

Example 7

Figure 9:
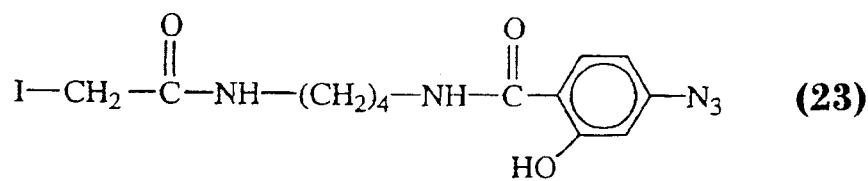
FIG. 9 is a flow chart which illustrates the preparation and use of an anti-adhesion composition comprising collagen and the anti-adhesion binding agent ASIB, and the analogous compound APDP.
Figure 9:
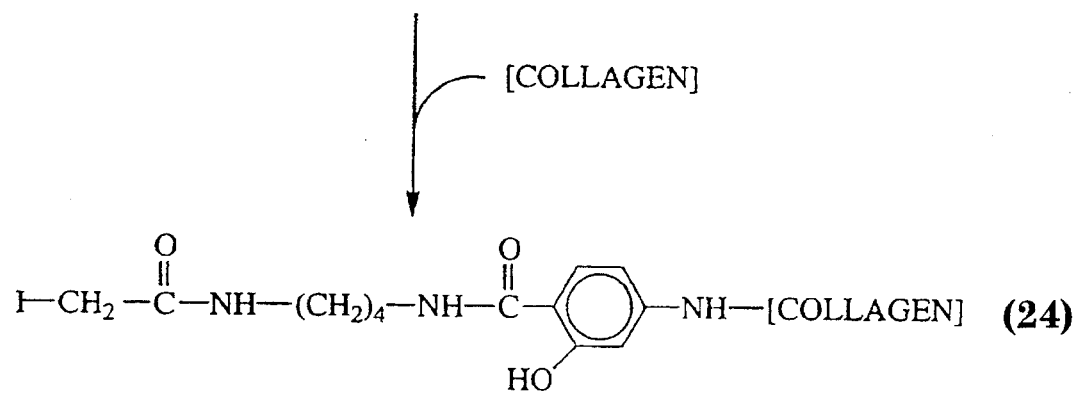
Figure 9:
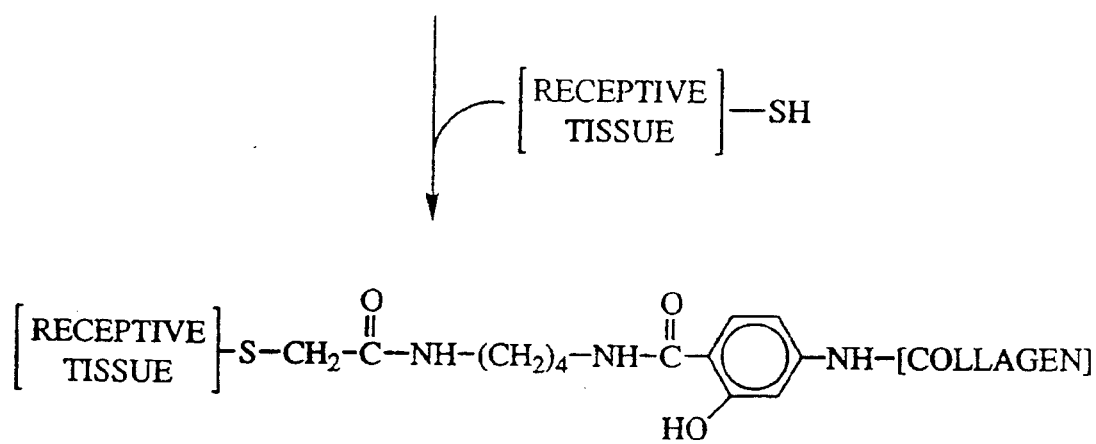
Figure 9:
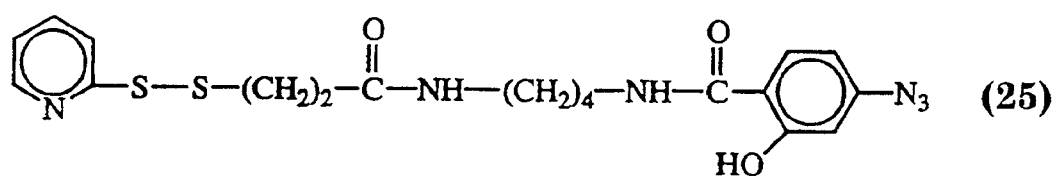

Use of an Anti-Adhesion Binding Agent With "Azido" and "Haloacetyl" Groups: ASIB A flow chart which illustrates the preparation and use of an anti-adhesion binding composition comprising the titled anti-adhesion binding agent is shown in FIG. 9. ASIB (1-(p-azidosalicylamido)-4-(iodoacetamido)butane, Compound 23) is first reacted with collagen. The azide group of the ASIB, acting as a collagen-reactive functional group, is heat or light activated to yield a highly reactive —N group (and the by-product, gaseous nitrogen), which reacts with chemical bonds found in collagen (including, for example, C—H and C=C) to form secondary amine linkages (—NH—) (yielding the anti-adhesion composition, Compound 24) or with carbon-carbon double bonds (C=C) found in collagen to form a cyclic aziridine-like linkage (e.g., —N[—C—C—]). This anti-adhesion composition, Compound 24, is then reacted with receptive tissue. The iodoacetyl group of the ASIB moiety (e.g., possessing a haloacetyl group), acting as a tissue-selective group, reacts with free sulfhydryl groups (—SH) found in compounds of receptive tissue (for example, fibrin or other sulfhydryl-containing tissue macromolecule) at pH 6.5 to 7.5 to form a covalent sulfide linkage (—S—) to the tissue compounds. Again, the by-product, iodide ion, is nominally non-toxic. Other haloacetyl groups may be used as tissue-selective groups, such as bromoacetyl and chloroacetyl groups.

Yet another anti-adhesion binding agent, APDP (N-[4-(p-azidosalicylamido) butyl]-3'-(2'-pyridyldithio)propionamide, Compound 25), which possesses "disulfide" and "azide" groups, may be used in an analogous manner to obtain results similar to those for other disulfide and azide groups described above.

What is claimed is:

1. An anti-adhesion composition for treatment of receptive tissue comprising:
   (i) a substrate material; and
   (ii) an anti-adhesion binding agent, wherein said anti-adhesion agent further comprises a substrate-reactive functional group and a tissue-selective functional group.

2. The anti-adhesion composition of claim 1, wherein said substrate material comprises collagen.

3. The anti-adhesion composition of claim 1, wherein said tissue-selective group is a sulfhydryl-selective functional group.

4. The anti-adhesion composition of claim 2, wherein said binding agent comprises a derivative of polyethylene glycol.

5. The anti-adhesion composition of claim 3, wherein said sulfhydryl-selective functional group is selected from the group consisting of:
   (i) a disulfide group;
   (ii) a haloacetyl group;
   (iii) a halomethyl ester group;
   (iv) a β-Nitrovinyl group;
   (v) an N-hydroxy succinimidyl ester group; and
   (vi) a maleimidyl group.

6. The anti-adhesion composition of claim 5, wherein said sulfhydryl-selective functional group is selected from the group consisting of:
   (i) a disulfide group;
   (ii) a haloacetyl group;
   (iii) a halomethyl ester group; and
   (iv) a β-Nitrovinyl group.

7. The anti-adhesion composition of claim 6, wherein said sulfhydryl-selective functional group is a disulfide group.

8. The anti-adhesion composition of claim 7, wherein said disulfide group is a 2-pyridinyl-disulfide group or a 3-carboxylic acid-4-nitro-phenyl-disulfide group.

9. The anti-adhesion composition of claim 5, wherein said substrate-reactive functional group is selected from the group consisting of:
   (i) an active ester group;
   (ii) a haloacetyl group;
   (iii) an azide group;
   (iv) a haloformate group;
   (v) a sulfonyl halide group;
   (vi) an isocyanate group;
   (vii) an isothiocyanate group;
   (viii) an acid anhydride group;
   (ix) an acid halide group; and
   (x) an imidate ester group.

10. The anti-adhesion composition of claim 5, wherein said substrate-reactive functional group is selected from the group consisting of:
    (i) an active ester group;
    (ii) a haloacetyl group; and
    (iii) an azide group.

11. The anti-adhesion composition of claim 1, wherein said tissue-selective functional group is an amine-selective functional group.

12. The anti-adhesion composition of claim 1, wherein said tissue-selective functional group is an active ester group.

13. The anti-adhesion composition of claim 2, wherein said tissue-reactive functional group is an active ether group.

14. The anti-adhesion composition of claim 11, wherein said amine-selective functional group is selected from the group consisting of an active ester group, an active ether group, and combinations thereof.

15. The anti-adhesion composition of claim 4, wherein said substrate-reactive functional group is an active ester group.

16. The anti-adhesion composition of claim 4, wherein said substrate-reactive functional group is an active ether group.

17. The anti-adhesion composition of claim 5 wherein said substrate-reactive functional group is an N-succinimidyl active ester group or a 2,4-dinitrophenyl active ester.

18. An anti-adhesion device for treatment of receptive tissue, said device comprising at least one layer of substrate material covalently bonded to an anti-adhesion binding agent, wherein said anti-adhesion agent further comprises a tissue-selective functional group.

19. The anti-adhesion device of claim 18, wherein receptive tissue to which said device is to be covalently bonded has been treated to convert disulfide groups or primary amino groups on the surface of said tissue to sulfhydryl groups prior to covalent bonding of said substrate material to said tissue.

20. The anti-adhesion device of claim 18 or claim 19, wherein said substrate material comprises collagen.

21. The anti-adhesion device of claim 18, wherein said tissue-selective group is a sulfhydryl-selective group.

22. The anti-adhesion device of claim 18, wherein said tissue-selective functional group is an amine-comprising group.

23. The anti-adhesion device of claim 18 or claim 19, wherein said binding agent comprises a derivative of polyethylene glycol.

24. A method for preventing the formation of an adhesion, comprising the steps of:

(i) providing the anti-adhesion device of claim 18 or claim 19; and (ii) covalently bonding said anti-adhesion device to receptive tissue.

* * * * *